United States Patent [19]
Moore et al.

[11] Patent Number: 5,908,617
[45] Date of Patent: Jun. 1, 1999

[54] MILD SHOWER GEL COMPOSITION COMPRISING UNIQUE THICKENER SYSTEM WHICH IMPARTS IMPROVED LATHERING PROPERTIES AND MODIFIED RINSE FEEL

[75] Inventors: Christine June Moore; Everett Junior Inman, both of Cincinnati; Timothy James Welch, West Chester; Charles Kevin Schell, Loveland, all of Ohio

[73] Assignee: The Procter & Gamble Company, Cincinnati, Ohio

[21] Appl. No.: 08/675,137

[22] Filed: Jul. 3, 1996

Related U.S. Application Data

[63] Continuation of application No. 08/295,124, Aug. 24, 1994, Pat. No. 5,607,678.

[51] Int. Cl.$^6$ ............................... A61K 7/48; A61K 7/50
[52] U.S. Cl. .................................... 424/70.19; 424/70.13; 514/846
[58] Field of Search ............................... 424/70.1, 70.19, 424/70.13; 514/846

[56] References Cited

U.S. PATENT DOCUMENTS

| | | | |
|---|---|---|---|
| 5,290,471 | 3/1994 | Greene | 252/108 |
| 5,326,483 | 7/1994 | Halloran | 252/174.15 |

*Primary Examiner*—Sally Gardner-Lane
*Attorney, Agent, or Firm*—Darryl C. Little; Tara M. Rosnell; George W. Allen

[57] ABSTRACT

A mild liquid skin cleanser composition with improved lathering and rinsing characteristics, comprising: an alkyl ethoxylated sulfate anionic surfactant having an average degree of ethoxylation of at least about 2.0; an amphoteric surfactant selected from the group consisting of betaine surfactants, imidazoline surfactants, aminoalkanoate surfactants, and iminodialkanoate surfactants, and mixtures thereof; an N-acylamino acid surfactant, or salt thereof; a cationic cellulose ether derivative; from 0.2 parts to 2.0 parts by weight of a C8 to C20 fatty alcohol; and from 0.1 parts to 5 parts by weight of a water insoluble salt of C14–C22 fatty acid.

9 Claims, No Drawings

5,908,617

MILD SHOWER GEL COMPOSITION COMPRISING UNIQUE THICKENER SYSTEM WHICH IMPARTS IMPROVED LATHERING PROPERTIES AND MODIFIED RINSE FEEL

This is a continuation of application Ser. No. 08/295,124, filed on Aug. 24, 1994 now U.S. Pat. No. 5,607,678.

TECHNICAL FIELD

The present invention is related to mild liquid personal cleanser compositions. More specifically, the present invention relates to mild, high lathering compositions with modified rinse feel attributes targeted for all-body use as shower gels.

BACKGROUND OF THE INVENTION

The cleaning of skin with surface-active cleansing preparations is the basis for the personal cleansing consumer market world-wide. Many people wash their skin with various surface-active preparations several times a day, with frequent whole body exposure to these compositions (e.g. bathing or showering). Traditionally, consumers were offered these cleansing compositions in the form of a solid "bar" comprised of either alkali earth salts of fatty acids (soap) or mixed synthetic surfactant/soap systems. While these products provide acceptable cleansing of skin and performance properties (e.g. lather), they possess certain properties which give rise to specific consumer negatives in terms of product messiness during use and irritation to skin (e.g. drying). These specific consumer negatives have been partially addressed through the introduction of liquid personal cleanser compositions in the form of shower gels. However, these shower gel products while addressing messiness and mildness needs of the consumer, often fail to meet other consumer performance needs, specifically high lather and soap-like rinse feel. A shower gel composition delivering high mildness, high lather, and rinsing properties more soap-like would be very desirable.

Skin cleansing compositions should lather and rinse, cleanse the skin gently, causing little or no irritation, without drying the skin after frequent routine use. Certain synthetic surfactants and surfactant systems formulated for skin cleansing are particularly mild, however, they possess poor lather performance and slick rinse-feel attributes. Other surfactants and surfactant systems (for example, soap-based system) provide good lather and rinsing performance, but are not exceptionally mild to the skin. Additionally, these formulations require a thickening agent, often some polymeric component, along with high levels of salt to produce consumer acceptable product viscosities. This thickening approach can cause the product to exhibit dramatic viscoelastic properties during use and impact other product performance attributes (e.g. ease of lathering). In addition, polymeric thickeners can be costly and exhibit base odors.

Optimization of any single product attribute (e.g. lather, mildness, rinse feel, viscosity), is a relatively straightforward process. There are numerous combinations of surfactants and other components which can be utilized to generate a product which delivers against any of the aforementioned attributes. The use of known high sudsing anionic surfactants with lather boosters yields acceptable lather volume. Unfortunately, highest sudsing anionic surfactants are, generally, also highest in skin irritation and, hence, worst in clinical mildness. Surfactants that are among the mildest with minimal skin irritation, such as ammonium lauryl ether (12EO) sulfate (NH4AE12S) are extremely poor in lather. These two facts alone make the selection of surfactants for optimization of lather performance, in and of itself, a delicate balancing act and becomes even more complex when the other product attributes must be optimized as well. See, e.g., U.S. Pat. Nos. 4,338,211, Stiros, issued Jul. 6, 1982; 4,310,433, Stiros, issued Jan. 12, 1982; and 4,842,850, Vu, issued Jun. 27, 1989, all of said patents being incorporated herein by reference.

In short, mildness is often obtained at the expense of effective cleansing and lathering. In addition, these mild formulations often come at the expense of other consumer preferred product performance attribute, such as bar soap-like rinse feel Finally, the thickening of these mild formulations also results in product viscoelastic properties which are non-ideal.

OBJECTS OF THE PRESENT INVENTION

The present invention offers a valuable combination of desirable properties to liquid skin-cleansing formulations in terms of product mildness, lathering, and rinse-feel.

Therefore, one object of this invention is the development of liquid skin-cleansing compositions which exhibit good mildness with good cleaning and improved lathering in terms of both amount and creaminess.

Another object of the present invention is the development of low cost liquid skin cleansers which deliver rinse-feel attributes more similar to that experience with bar soap usage.

Another object of the present invention is the development of a thickening system which delivers improved lathering and rinse-feel profiles while not imparting dramatic product viscoelastic properties nor having a deleterious effect on mildness or other product attributes.

Other objects will become apparent from the detailed description below.

SUMMARY OF THE INVENTION

A mild liquid skin cleanser composition with improved lathering and rinsing characteristics, comprising: an allyl ethoxylated sulfate anionic surfactant having an average degree of ethoxylation of at least about 2.0; an amphoteric surfactant selected from the group consisting of betaine surfactants, imidazoline surfactants, aminoalkanoate surfactants, and iminodialkanoate surfactants, and mixtures thereof; an N-acylamino acid surfactant, or salt thereof; a cationic cellulose ether derivative; from 0.2 parts to 2.0 parts by weight of a C8 to C20 fatty alcohol; and from 0.1 parts to 5 parts by weight of a water insoluble salt of C14–C22 fatty acid.

DETAILED DESCRIPTION OF THE INVENTION

A liquid skin cleanser composition with improved mildness and lathering characteristics, comprising:
 (a) from about 3 parts to about 10 parts, by weight, of an alkyl ethoxylated sulfate anionic surfactant having an average degree of ethoxylation of at least about 2.0;
 (b) from about 3 parts to about 10 parts of an amphoteric surfactant selected from the group consisting of betaine surfactants, imidazoline surfactants, aminoalkanoate surfactants, and iminodialkanoate surfactants, and mixtures thereof;
 (c) from about 0.1 parts to about 3 parts, by weight of an N-acylamino acid surfactant, or salt thereof, (d) from about 0.01 parts to about 0.5 parts, by weight of the composition, of a cationic cellulose ether derivative, (e) water from 50 parts to 94 parts, and preferably from 76 parts to 90 parts, (f) from 0.2 parts to 2.0 parts by weight of a C8 to C20 fatty alcohol, and (g) from 0.1 parts to 5 parts by weight of a water insoluble salt of C14–C22 fatty acid, wherein said personal cleansing composition is substantially free of traditional polymeric thickeners and there is little or no alkyl sulfate anionic surfactant.

A preferred mild liquid personal cleansing composition comprises:

| | Parts, by weight |
|---|---|
| A preferred mild liquid personal cleansing composition comprises: | |
| Cocamidopropyl Betaine | 4–6 |
| Sodium Laureth Sulfate | 5–7 |
| Sodium Lauroyl Sarcosinate | 0.3–0.7 |
| Polyquaternium 10 | 0.05–0.2 |
| C12/14 Fatty Alcohol | 0.25–0.75 |
| Zinc Stearate | 1–2 |
| Glycol Distearate | 0.2–0.4 |
| Sodium Lauryl Sulfate | 0.4–0.6 |
| Cocamidopropyl Betaine | 0.1–0.3 |
| Lauramide DEA | 0.3–0.6 |
| Sodium Sulfate | 0.05–1.5 |
| Citric Acid | 0.05–0.2 |
| DMDM Hydantoin | 0.2 |
| Tetra Sodium EDTA | 0.1 |
| Fragrance | 0.2–1.0 |
| Water | Q.S. |
| Viscosity (cps) | 5,000–11,000. |
| A highly preferred mild liquid personal cleansing composition is: | |
| Cocamidopropyl Betaine | 5.15 |
| Sodium Laureth Sulfate | 5.8 |
| Sodium Lauroyl Sarcosinate | 0.5 |
| Polyquaternium 10 | 0.1 |
| C12/14 Fatty Alcohol | 0.45 |
| Zinc Stearate | 1.5 |
| Glycol Distearate | 0.25 |
| Sodium Lauryl Sulfate | 0.53 |
| Cocamidopropyl Betaine | 0.17 |
| Lauramide DEA | 0.48 |
| Sodium Sulfate | 0.05–1.5 |
| Citric Acid | 0.05–0.2 |
| DMDM Hydantoin | 0.2 |
| Tetra Sodium EDTA | 0.1 |
| Fragrance | 0.2–1.0 |
| Water | Q.S. |
| Viscosity (cps) | 5,000–11,000. |

The invention, including preferred embodiments thereof, is described in more detail in the Detailed Description of the Invention, which follows.

The essential as well as a variety of optional components of the compositions of the present invention are described below.

C8 to C20 Fatty Alcohol

The mild personal liquid cleanser composition hereof comprises from about 0.2 to 2.0 parts, by weight, preferably from about 0.2 to 1.0 parts of fatty alcohol of the formula RCH2 OH wherein R is an alkyl from about 7 to 19 carbons, preferably from 9 to 17 carbons, more preferably from 11 to 13 carbons.

Fatty alcohols are known in the shampoo art for viscosity building and foam stabilization. In the present invention, fatty alcohol is part of the thickening system which enables the elimination of traditional polymeric thickeners. In addition, fatty alcohol increases the creaminess of lather by increasing efficiency of surfactant packing. However, at high levels fatty alcohol will be a load on lather amount.

Water Insoluble Fatty Acid Salt

The mild personal liquid cleanser composition hereof comprises from about 0.1 to 5 parts, by weight, preferably 0.2 to 3 parts, more preferably from 0.5 to 2 parts of water-insoluble fatty acid salts.

Water-insoluble fatty acid salts suitable for use herein include zinc, magnesium calcium, and aluminum salts of C14–C22, preferably C16–C18 fatty acids, and mixtures thereof. Highly preferred from the viewpoint of lather and draggy rinse-feel are the zinc salts, especially zinc salts of C16–C18 fatty acids which are marketed under the designation zinc stearate. The water-insoluble fatty acid salt are especially valuable in combination with fatty alcohol for viscosity building and lather enhancement. Zinc stearate will offset any slick feel or lather load caused by fatty alcohol.

Alkyl Ethoxylated Sulfate

The mild personal liquid cleanser composition hereof comprises from about 3 parts to about 10 parts, by weight, preferably from about 4 parts to about 8 parts of alkyl ethoxylated sulfate anionic surfactant.

Alkyl ethoxylated sulfate surfactants are well known in the art, and can be represented by the formula $RO(C_2H_4O)_xSO_3M$, wherein R is alkyl or alkenyl of from about 8 to about 24 carbon atoms, x is 1 to 12, preferably 2 to 6, and M is a water-soluble cation such as an alkali or alkaline earth metal, preferably, sodium or potassium. The average degree of ethoxylated, i.e. the average value for x should be at least about 2.0.

Exemplary alkyl ethoxylated sulfates are condensation products of ethylene oxide and monohydric alcohols having from about 8 to about 24 carbon atoms. Preferably, R has from about 10 to about 18 carbon atoms. The alcohols can be derived from fats, e.g., coconut oil or tallow, or can be synthetic. Lauryl alcohol and straight chain alcohols derived from coconut oil are preferred herein. Such alcohols are typically reacted with from about 2 to about 12, preferably about 2 to about 6, more preferably about 3, molar proportions of ethylene oxide and the resulting mixture of molecular species having, for example, an average moles of ethylene oxide per mole of alcohol also within the above limits, is sulfated and neutralized.

Specific examples of alkyl ethoxylated sulfates which may be used in the present invention are the salts, especially sodium and/or potassium salts, of coconut alkyl triethylene glycol ethoxylated sulfate, tallow alkyl triethylene glycol ethoxylated sulfate, and tallow alkyl hexaoxyethylene sulfate. Typically the alkyl ether sulfates will comprise a mixture of individual compounds, said mixture preferably having an average alkyl chain length of from about 10 to about 16 carbon atoms, and an average degree of ethoxylation of from about 2 to about 6 moles of ethylene oxide. Especially preferred are narrow range alkyl ethoxylated sulfates such as those having ethoxylation levels primarily in the range of about 2 to about 6.

Amphoteric Surfactant

The amphoteric surfactant will be present in the mild personal liquid cleanser compositions hereof at levels of from about 3 parts to about 10 parts, by weight of the composition, preferably from about 4 parts to about 8 parts. The amphoteric component hereof is selected from the group consisting of amphoteric betaine, imidazoline, aminoalkanoate, and iminodialkanoate surfactants. Preferably, the ratio of the alkyl ethoxylated surfactant to the amphoteric surfactant will be from about 3:1 to about 1:1.5, more preferably from about 1.5:1 to about 1:1.5.

The imidazoline amphoteric surfactants hereof are depicted by Formula I:

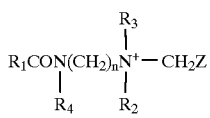
(I)

wherein $R_1$ is $C_8$–$C_{22}$ alkyl or alkenyl, preferably $C_{12}$–$C_{16}$, $R_2$ is hydrogen or $CH_2CO_2M$, $R_3$ is $CH_2CH_2OH$ or $CH_2CH_2OCH_2CH_2COOM$, $R_4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal or alkaline earth metal. Examples of "alkali metal" include lithium, sodium, and potassium. Examples of "alkaline earth metal" include beryllium, magnesium, calcium, strontium, and barium. This type of surfactant is classified herein as an "imidazoline" amphoteric surfactant for convenience, although it should be recognized that it does not necessarily have to be derived, directly or indirectly, through an imidazoline intermediate.

Suitable materials of this type are marketed under the tradename MIRANOL and are understood to comprise a complex mixture of species, and can exist in protonated and non-protonated species depending upon pH with respect to species that can have a hydrogen at $R_2$. All such variations and species are meant to be encompassed herein.

Preferred surfactants of Formula I are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate (alternately, cocoamphomonoacetate).

Specific commercial products providing the amphoteric surfactant component of the present compositions include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Suitable betaine surfactants hereof are depicted by compounds having the Formula (II):

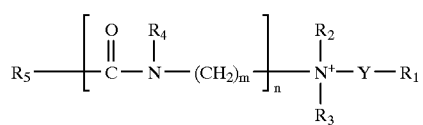
(II)

wherein:
$R_1$ is a member selected from the group consisting of

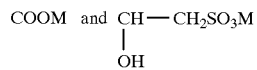

$R_2$ is lower alkyl or hydroxyalkyl;
$R_3$ is lower alkyl or hydroxyalkyl;
$R_4$ is a member selected from the group consisting of hydrogen and lower alkyl;

$R_5$ is higher alkyl or alkenyl;
Y is lower alkyl, preferably methyl;
m is an integer from 2 to 7, preferably from 2 to 3;
n is the integer 1 or 0;
M is hydrogen or a cation, such as an alkali metal or alkaline earth metal.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like.

Examples of surfactant betaines of Formula II wherein n is zero which are useful herein include the allylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Amido betaines and amidosulfo betaine surfactants useful in the present invention are exemplified by compounds of Formula II wherein n is one but otherwise corresponding to the above examples. Examples of surfactant betaines of Formula II wherein n is one which are useful herein include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, laurylamido-bis-(2-hydroxyethyl)-sulfopropylbetaine, and the like.

The preferred betaine in the present invention is a member selected from the group consisting of surfactant amidocarboxybetaines and amidosulfobetaines. More preferred betaines are the surfactant amidocarboxybetaines, particularly cocoamidodimethylcarboxymethylbetaines (cocomidopropylbetaine), such as those sold by Goldschmidt Co. under the trade name Tegobetaine (F grade), and by Hoechst-Celanese under the trade name Genagen CAB. These most preferred betaines have the formula:

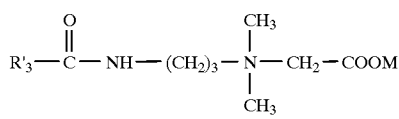

wherein $R'_3$ is selected from C8 to C18 alkyl radicals and M is hydrogen or a cation as defined above. In general, the preferred betaines hereof will have low levels of residual amide and sodium monochloroacetate.

Suitable aminoalkanoates and iminodialkanoates are represented by the Formulas (III and (IV):

aminoalkanoates of the formula:

iminodialkanoates of the formula:

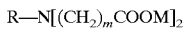

wherein n and m are from 1 to 4, R is $C_8$–$C_{22}$ alkyl or alkenyl, and M is hydrogen or alkali or an alkaline earth metal as previously described.

Examples of amphoteric surfactants falling within the aminoalkanoate formula include n-alkylamino-propionates and n-alkyliminodipropionates. Such material are sold under the tradename DERIPHAT by Henkel and MIRATANE by Miranol, Inc. Specific examples include N-lauryl-beta-amino propionic acid or salts thereof, and N-lauryl-beta-imino-dipropionic acid (DERIPHAT 160C) or salts thereof, and mixtures thereof N-Acylamino Acid Surfactant The mild personal liquid cleanser compositions of the present invention comprise from about 0.1 parts to about 3 parts, preferable from about 0.25 parts to about 1 parts of N-acyl amino acid surfactant.

N-acyl amino acid surfactants, for purposes hereof, include N-acyl hydrocarbyl acids and salts thereof, such as those represented by Formula V, as follows:

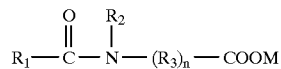

wherein: $R_1$ is a $C_8$–$C_{24}$ alkyl or alkenyl radical, preferably $C_{12}$–$C_{18}$; $R_2$ is —H, $C_1$–$C_4$ alkyl, phenyl, or —$CH_2COOM$, preferably $C_1$–$C_4$ alkyl, more preferably $C_1$–$C_2$ alkyl; $R_3$ is —$CR^4_2$— or $C_1$–$C_2$ alkoxy, wherein each $R^4$ independently is —H or $C_1$–$C_6$ alkyl or alkylester, and n is from 1 to 4, preferably 1 or 2; and M is —H or a cation as previously defined, preferably an alkali metal such as sodium or potassium.

A wide variety of N-acyl acid surfactants and their synthesis are described in *Anionic Surfactants, Part II, Surfactant Science Series, Vol. VII*, edited by Warner M. Linfield, Marcel Dekker, Inc. (New York and Basel), 1976; pp 581–617.

Especially preferred are compounds of Formula V wherein $R_2$ is methyl and $R_3$ is —$CH_2$—, an n is 1, which are known as the N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms.

For the purposes of the surfactants described herein, it should be understood that the terms "alkyl" or "alkenyl" include mixtures of radicals which may contain one or more intermediate linkages such as ether or polyether linkages or non-functional substitutents such as hydroxyl or halogen radicals wherein the radical remains of hydrophobic character.

Cationic Cellulose Ether Derivatives

The mild personal liquid cleanser compositions of the present invention comprise from about 0.01 parts–to 0.5 parts, preferable from 0.02 parts–to 0.2 parts of a cationic cellulose ether derivative.

Cationic cellulose ether derivatives, for purposes hereof, is a polymeric quaternary ammonium salt of hydroxyethyl cellulose reacted with a trimethyl ammonium substituted epoxide.

Foam enhancers are well known in the art. Polyquaternium-10 (an industry term designated by the Cosmetic, Toiletry and Fragrance Association (CFTA) for a polymeric quaternary ammonium salt of hydroxyethyl cellulose reacted with a trimethyl ammonium substituted epoxide is a prefered polymer for foam enhancement. In addition, polyquaternium-10 has also been shown in prior art to provide a skin mildness benefit by reducing irritation potential of the surfactant. Polyquaternium-10 is commercially available from Union Carbide Corp. (Danbury, Conn., USA) under their UCARE POLYMER JR series of materials, e.g., UCARE POLYMER JR-30M, JR-125, and JR400.

Water

The mild personal liquid cleanser composition hereof will also comprise water. Generally, the composition will contain from about 50 parts to about 94 parts water, and preferably about 76 parts to about 90 parts water.

Mild Personal Liquid Cleanser Compositions

The mild personal liquid cleanser hereof is substantially free of alkyl sulfate surfactants since alkyl sulfates are relatively harsh to the skin. It is recognized that there will generally be some alkyl sulfate present as a result of it being present in commercially available allyl ethoxylated sulfate raw materials. For example, commercially available alkyl (3) ethoxylated sulfate typically contains about 20 parts by weight alkyl sulfate; commercially available alkyl (2) ethoxylated sulfate, about 25 parts to about 40 parts alkyl sulfate. For purposes hereof, substantially free of alkyl sulfate means the compositions hereof should have an alkyl sulfate:alkyl ethoxylated sulfate (average degree of ethoxylation of 2.5 and above) weight ratio of no more than about 0.35, preferably no more than about 0.30, more preferably no more than about 0.25. For alkyl ethoxylated sulfate with an average ethoxylation level of less than 2.5, the ratio should be no more than about 0.40, preferably no more than about 0.35, more preferably no more than about 0.30, most preferably no more than about 0.25. It is preferred that no additional amount of alkyl sulfate be added other than that which occurs inherently with the alkyl ethoxylated sulfate.

Narrow range ethoxylates can be used to lower the alkyl sulfate:alkyl ethoxylated sulfate weight ratio. "Narrow range ethoxylates" refer to alkyl ethoxylated sulfate surfactants that have been processed to reduce alkyl sulfates and, optionally, alkyl ethoxylated sulfates outside of the desired range of ethoxylation. The use of narrow range ethoxylates can be used to lower the alkyl sulfate:alkyl ethoxylated sulfate weight ratio, including to ratios as low as about 0.2 or even about 0.1, and less.

It is also acceptable for alkyl sulfates to come into the composition as part of the pearlescent agent pre-mix (for aesthetics) at final composition levels below 1.0 parts weight.

It is also preferred that no other ingredients that are unduly harsh to the skin be added to the mild mild personal liquid cleanser compositions hereof.

Additional Ingredients

The compositions of the present invention can contain a wide variety of optional ingredients useful or known for use in the art for hand soaps and other mild personal liquid cleanser compositions. Exemplary additional ingredients are described below.

Additional surfactants that can be used include other anionic, nonionic, and amphoteric surfactants, as well as zwitterionic and cationic surfactants.

Anionic Surfactants

A suitable class of anionic surfactants are the water-soluble, organic salts of the general formula:

$$R_1\text{—}SO_3\text{—}M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal sulfonated $C_{12-18}$ paraffins.

Additional examples of anionic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278; incorporated by reference.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

Another class of anionic surfactants are the b-alkyloxy alkane sulfonates. These compounds have the following formula:

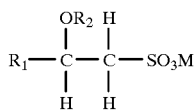

where $R_1$ is a straight chain alkyl group having from about 6 to about 20 carbon atoms, $R_2$ is a lower alkyl group having from about 1 (preferred) to about 3 carbon atoms, and M is a water-soluble cation.

Many additional synthetic anionic surfactants are described in *McCutcheon's. Emulsifiers and Detergents*, 1989 *Annual*, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference. Soaps, of course, also fall within the scope of anionic detersive surfactants that can be used.

Nonionic Surfactants

A wide variety of nonionic surfactants can be used. Nonionic surfactants include those broadly defined as compounds produced by the condensation of alkylene oxide groups (hydrophilic in nature) with an organic hydrophobic compound, which may be aliphatic or alkyl aromatic in nature. Examples of classes of nonionic surfactants are:

1. The polyethylene oxide condensates of alkyl phenols, e.g., the condensation products of alkyl phenols having an alkyl group containing from about 6 to about 20 carbon atoms, preferably from about 6 to about 12, in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40 parts to about 80 parts polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N\rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P\rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polysorbates, e.g., sucrose esters of fatty acids. Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

8. Alkyl polysaccharide nonionic surfactants are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. The polysaccharide can contain from about 1.0 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentagluscosides and tallow alkyl, tetra-, penta-, and hexaglucosides.

9. Polyethylene glycol (PEG) glyceryl fatty esters, as depicted by the formula $RC(O)OCH_2CH(OH)CH_2(OCH_2CH_2)_nOH$ wherein n is from about 5 to about 200, preferably from about 20 to about 100, more preferably from about 30 to about 85, and RC(O)— is an ester wherein R comprises an aliphatic radical having from about 7 to 19 carbon atoms, preferably from about 9 to 17 carbon atoms, more preferably from about 11 to 17 carbon atoms, most preferably from about 11 to 14 carbon atoms. The combinations of n from about 20 to about 100, with $C_{12}$–$C_{18}$, preferably $C_{12}$–$C_{15}$ fatty esters, for minimized adverse effect on foaming, is preferred.

Suitable glyceryl fatty ester portions of these surfactants include glyceryl cocoate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil.

Other surfactants that can be used include soluble cationic surfactants, such as quaternary ammonium surfactants, and other amphoteric and zwitterionic surfactants known to those in the art.

Conditioning Agent

Optional components include from 0.1 to 1.5 parts of conditioning agents such as vegetable oils prepared from non-conjugated polyunsaturated fatty esters which are conjugated and elaidinized then modified by Dies-Alder addition with a member of the group consisting of acrylic acid, fumaric acid and maleic anhydride. The adducts and their preparation are described in U.S. Pat. No. 4,740,367, Force, et al., Apr. 26, 1988, incorporated herein by reference, the adducts being marketed under the trade name Ceraphyl GA (Van Dyke). Preferred vegetable oil adducts are those prepared from soybean oil and adducts derived by Dies-Alder addition of vegetable oils with fumaric acid. A preferred method of preparing adducts herein is to react two moles of vegetable oil with one mole of the dienophile in the presence of catalytic amounts of iodine, the conjugation and elaidinization agent. This produces a 50:50 blend of adduct together with the disproportionated (conjugated) vegetable oil.

Another component includes the addition of petrolatum. Petrolatum can be any grade of white or yellow petrolatum recognized in the art as suitable for human application. The preferred type is USP Class III with a melting point between 122 and 135° F. (50 and 57° C.). Such a material is commercially available as Penreco Snow White Pet USP. The petrolatum in this invention includes hydrocarbon mixtures formulated is with mineral oils in combination with paraffin waxes of various melting points. Preferred conditioning agents of this type are disclosed in U.S. patent application Ser. No. 07/909,834, Dias, et al., filed Jul. 7, 1992, and U.S. patent application Ser. No. 07/909,877, Kacher, et al., filed Jul. 7, 1992, allowed and incorporated herein by reference.

Examples of other moisturizers include the water soluble hexadecyl, myristyl, isodecyl or isopropyl esters of adipic, lactic, oleic, stearic, myristic or linoleic acids, as well as many of their corresponding alcohol esters (sodium isostearoyl-2-lactylate, sodium capryl lactylate), polyethyleneglycol esters such as PEG (6) caprylic/capryl glycerate (Softigan 767), hydrolyzed protein and other collagen-derived proteins, aloe vera gel and acetamide MEA.

An optional component hereof is a soluble conditioning agent suitable for conditioning hair or skin. Skin conditioning proteolytic enzyme can also be used.

Suitable conditioners include, for example, soluble polyether siloxane copolymer, such as a polypropylene oxide modified dimethylpolysiloxane (e.g., Dow Corning DC-1248), although ethylene oxide or mixtures of ethylene oxide and propylene oxide may also be used. The ethylene oxide and polypropylene oxide level must be sufficiently high to provide solubility in water and the composition hereof.

Antibacterial Agent

The antibacterial agent when used can be present at a level of from about 0.01% to about 4%, typically from about 0.1% to about 2%, and preferably from about 0.5% to about 1%. The level is selected to provide the desired level of antibacterial activity and can be modified as desired. The preferred antibacterial agent is 2-hydroxy-4,2',4'-trichlorodiphenylether (TCS). Other halogenated antibacterial agents are set out below. Many antibacterial agents, known to those skilled in the art and disclosed in, e.g., U.S. Pat. Nos. 3,835,057 and 4,714,563, both incorporated hereinbefore by reference, may be used.

Suitable antibacterial agents include:
2-hydroxy-4,2',4'-trichlorodiphenylether (TCS);
2,6-dimethyl-4-hydroxychlorobenzene (PC);
3,4,4'-trichlorocarbanilide (TCC);
3-trifluoromethyl-4,4'-dichlorocarbanilide (TFC);
2,2'-dihydroxy-3,3',5,5',6,6'-hexachlorodiphenylmethane;
2,2'-dihydroxy-3,3',5,5'-tetrachlorodiphenylmethane;
2,2'-dihydroxy-3,3'dibromo-5,5'-dichiorodiphenylmethane;
2-hydroxy-4,4'-dichlorodiphenylether;
2-hydroxy-3,5',4-tribromodiphenylether; and
1-hydroxyl-4-methyl-6-(2,4,4-trimethylpentyl)-2(1H)-pyridinone (Octopirox).

Sensates

Sensates when used can be present at a level of from about 0.01% to about 2%, typically from about 0.05% to about 1%, and preferably from about 0.1% to about 0.5%. The level is selected to provide the desired level of consumer perceived sensation and can be modified as desired. Suitable sensate technologies include menthol, eucalyptus, and Wilkinson Sword.

Other Optional Components

The skin cleansers herein can contain a variety of nonessential, optional ingredients suitable for improving such compositions in a variety of ways. Such conventional, optional ingredients are well known to those skilled in the art, e.g., antibacterial agents and preservatives such as DMDM Hydantoin, benzyl alcohol, methyl paraben, propyl paraben, 3-isothiazolines (Kathon CG sold by Rohm and Haas), imidazolidinyl urea, methylchloroisothiazolinone, and methylisothiazolinone can be used in amounts of from 1 to 5,000 ppm; final viscosity adjusters such as sodium sulfate, sodium chloride, propylene glycol; suspending agents such as magnesium/aluminum silicate; perfumes, dyes; opacifiers such as ethylene glycol distearate, glycol monostearate, styrene acrylate copolymer, mica, behenic acid, and calcium stearate; sequestering agents such as disodium ethlyenediamine tetraacetate; emollients, moisturizers and various other skin treating ingredients such as glycerin; buffers and builders such as citrates and phosphates. If present, such agents individually generally comprise from about 0.01% to about 5% by weight of the composition.

Body Sponge Implement

A body puff or sponge which is made of nylon mesh in the shape of a round sponge (about 4.5 inches in diameter) which when used in conjunction with this invention, is an effective system which enhances the delivery of mild skin cleansing and skin conditioning benefits. Such a puff is manufactured by the sponge factory (Bilange). The puff is comprised of three pieces of extruded tubular netting (scrim) which is folded numerous times to form a soft ball-like sponge, with a nylon rope attached. A suitable system of this type is disclosed in U.S. patent application Ser. No. 08/080, 668, filed Jun. 18, 1993, Gordon, et al. Similar sponges can also be used.

Preferences

This lists the preference levels of the raw materials from a low level to a mid level to a high level as used in the preferred liquid personal cleanser of the present invention:

Water/Solvent is low at 50–76 parts; medium at 76–90 parts and high at 90–94 parts.

Cocamidopropyl Betaine is an Amphoteric and is low at 3–4 parts; medium at 4–8 parts and high at 8–10 parts.

MES*/Anionic is low at 3–4 parts; medium at 4–8 parts and high at 8–10 parts.

* Mild etboxylated surfactants

N-acylamino acid surfactant/Anionic lather booster is: 0.1–0.25; 0.25–1; and 1–3 parts, respectively.

Polymer JR**/Polymeric lather booster is: 0.01–0.02; 0.02–0.2; and 0.2–0.5 parts respectively.

** A cationic cellulose etere derivative

Fatty alcohol thickener, lather creaminess enhancer is: low at 0.2–0.4; medium at 0.4–1.0; high at 1.0–2.0 parts respectively.

Zinc stearate/rinse-feel, lather booster, thickener is: low at 0.1–0.5; medium at 0.5–2; high at 2–5 parts respectively.

Minor ingredients are: Sodium Sulfate/viscosity adjuster, Citric Acid/pH adjuster, DMDM Hydantoin/Preservative, Tetra Sodium EDTA/Preservative, and Fragrance/Perfume.

METHOD OF USE

In its method aspect, the present invention comprises a method of washing the skin by contacting the skin with an amount of the cleanser compositions herein which is effective to clean the skin and rinsing the excess cleanser from the skin. An effective amount for any individual will depend upon variable factors such as amount of soil on the skin, type of soil on the skin, level of surfactant in the cleanser composition, etc. Generally, an effective amount will be from about 0.5 to about 7 grams per use. A preferred method of use is with the body sponge implement.

Shower Gel versus Shampoos

The exemplified compositions of the present invention would not be appropriate in the shampoo context because surfactant levels are too low to exhibit the cleaning effectiveness required by a shampoo.

PREFERRED METHOD OF PROCESSING

The compositions in the examples described in the section below were processed using the following method:

1. Slowly add polymer to water and evenly disperse using a jacketed mix tank with agitator.
2. Heat the polymer/water mixture to 65–75° C. with steam/water through the jacket.
3. Once temperature has been reached, immediately shut off heat source to mix tank.
4. Add the fatty alcohol to the hot polymer/water mixture while continuing to mix. If the fatty alcohol is added to an unheated mix, it will immediately solidify.
5. Immediately pump room temperature sodium laureth sulfate into the mixture while agitating. It will be necessary to increase agitator speed at this time to ensure proper mixing. Avoid aerating the mixture. Note: The addition of this surfactant and the following surfactants effectively reduce the temperature of the mixture in order to introduce the preservative system and perfume later on in the batch making process. It may be necessary to provide additional cooling (i.e. cold water through the crutcher jacket) in order to reduce batching time.

6. Add cocamidopropyl betaine. Mixture will thicken slightly. Increase agitator to mix without entrapping air.
7. Slowly add zinc stearate and disperse evenly using agitation. Mix thoroughly until all clumps and visible particles are broken up.
8. Reduce pH to 5.6–5.9 (neat) with the careful, slow addition of citric acid solution to reach isoelectric range of amphoteric surfactant. If each addition of citric acid is not allowed to react fully, it is easy to over acidify.
9. Add sodium lauroyl sarcosinate and EDTA.
10. Once mixture temperature is 36–40° C., add DMDM Hydantoin, perfume, and Pearlescent Agent pre-mix.
11. Check pH and adjust to 6.1 to 6.3 (neat).
12. Increase viscosity in increments to 5,000–11,000 cps with sodium sulfate. Allow sodium sulfate to fully dissolve and mix (~20 minutes) before taking each viscosity reading.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope.

Table 1

The compositions below show the effect of adding C12/14 fatty alcohol to a mild liquid personal cleansing composition which contains a traditional polymeric thickener.

Comparative Example 1: Mild liquid personal cleansing composition which contains a traditional polymeric thickener.

Experimental Examples 2, 3, and 4 are the said cleanser of Comparative Example 1 with the addition of 0.5, 1.0, and 2.0% fatty alcohol, respectively.

Key conclusions from the data are:
1. Fatty alcohol is an effective thickener. In the context with polyol alkoxy ester, fatty alcohol thickens the formula without the need for any sodium sulfate (see finished product viscosity data). In fact, using both the polymeric thickener and fatty alcohol together the compositions have higher viscosities than desired.
2. Fatty alcohol increases lather creaminess as measured by lather viscosity. The increase in creaminess levels off at about 2.0%.
3. Fatty alcohol becomes a load on lather amount at levels higher than 0.5%.

TABLE 1

|  | Comparative Example 1 | Experimental Example 2 | Experimental Example 3 | Experimental Example 4 |
| --- | --- | --- | --- | --- |
| Cocamidopropyl Betaine | 5.15 | 5.15 | 5.15 | 5.15 |
| Sodium Laureth Sulfate | 5.8 | 5.8 | 5.8 | 5.8 |
| Sodium Lauroyl Sarcosinate | 0.5 | 0.5 | 0.5 | 0.5 |
| Polyquaternium 10 | 0.1 | 0.1 | 0.1 | 0.1 |

TABLE 1-continued

|  | Comparative Example 1 | Experimental Example 2 | Experimental Example 3 | Experimental Example 4 |
| --- | --- | --- | --- | --- |
| Polyol Alkoxy Ester | 0.4 | 0.4 | 0.4 | 0.4 |
| C12/14 Fatty Alcohol | — | 0.5 | 1.0 | 2.0 |
| Sodium Sulfate | 2.1 | — | — | — |
| Citric Acid | 0.1 | 0.1 | 0.1 | 0.1 |
| DMDM Hydantoin | 0.2 | 0.2 | 0.2 | 0.2 |
| Tetra Sodium EDTA | 0.1 | 0.1 | 0.1 | 0.1 |
| Fragrance | 0.4 | 0.4 | 0.4 | 0.4 |
| Water | Q.S. | Q.S. | Q.S. | Q.S. |
| Finished Product Viscosity (cps) | 10,800 | 11,200 | 13,500 | 18,000 |
| Lather Viscosity (Ratio vs Comparative Example 1) | 1 | 2.8 | 4.5 | 3.8 |
| Hand Lather (mL) | 60 | 50 | 40 | 30 |
| Inverted Cylinder Lather (mL) | 356 | 307 | 294 | 239 |

Table 2

The compositions below show the effect of removing the traditional polymeric thickener and replacing with fatty alcohol in Experimental Example 5.

1. Fatty alcohol thickens the formula to the desired viscosity without the use of the polymeric thickener.
2. With fatty alcohol as primary thickener in Experimental Example 5, the lather creaminess is increased dramatically versus Comparative Example 1.

TABLE 2

|  | Comparative Example 1 | Experimental Example 5 |
| --- | --- | --- |
| Cocamidopropyl Betaine | 5.15 | 5.15 |
| Sodium Laureth Sulfate | 5.8 | 5.8 |
| Sodium Lauroyl Sarcosinate | 0.5 | 0.5 |
| Polyquaternium 10 | 0.1 | 0.1 |
| Polyol Alkoxy Ester | 0.3 | — |
| C12/14 Fatty Alcohol | — | 0.5 |
| Sodium Sulfate | 2.2 | 2.8 |
| Citric Acid | 0.1 | 0.1 |
| DMDM Hydantoin | 0.2 | 0.2 |
| Tetra Sodium EDTA | 0.1 | 0.1 |
| Fragrance | 0.2 | 0.2 |
| Water | Q.S. | Q.S. |
| Finished Product Viscosity (cps) | 9,380 | 8,470 |
| Expert User Panel* |  |  |
| Lather Amount (Ratio vs. Comparative Example 1) | 1 | 0.74 |
| Lather Creaminess (Ratio vs. Comparative Example 1) | 1 | 3.0 |

*Paired comparison test. Base = 15. Trained lather panelists lather their hands with the product and evaluate for lather amount and creaminess (Scale –3 to 3).

Table 3

The compositions below show the effect of changing the composition from clear (Experimental Example 5) to white pearlescent aesthetics with a higher perfume level Experimental Example 6).

1. The lather creaminess increase from the fatty alcohol is maintained upon changing from the clear liquid composition of Experimental Example 5 to the white pearlescent composition of Experimental Example 6.
2. The slight load o n lather from the fatty alcohol is offset by the low level of sodium lauryl sulfate which comes in with the Pearlescent Agent in Experimental Example 6.
3. The addition of fatty alcohol and change in aesthetics have not hurt the clinical mildness of the composition in Experimental Example 6 versus the Comparative Example 1.

TABLE 3

|  | Comparative Example 1 | Experimental Example 5 | Experimental Example 6 |
| --- | --- | --- | --- |
| Cocamidopropyl Betaine | 5.15 | 5.15 | 5.15 |
| Sodium Laureth Sulfate | 5.8 | 5.8 | 5.8 |
| Sodium Lauroyl Sarcosinate | 0.5 | 0.5 | 0.5 |
| Polyquaternium 10 | 0.1 | 0.1 | 0.1 |
| Polyol Alkoxy Ester | 0.3 | — | — |
| C12/14 Fatty Alcohol | — | 0.5 | 0.5 |
| Pearlescent Agent Pre-Mix: |  |  |  |
| Glycol Distearate | — | — | 0.25 |
| Sodium Lauryl Sulfate | — | — | 0.53 |
| Cocamidopropyl Betaine | — | — | 0.17 |
| Lauramide DEA | — | — | 0.48 |
| Sodium Sulfate | 2.2 | 2.8 | 0.73 |
| Citric Acid | 0.1 | 0.1 | 0.1 |
| DMDM Hydantoin | 0.2 | 0.2 | 0.2 |
| Tetra Sodium EDTA | 0.1 | 0.1 | 0.1 |
| Fragrance | 0.2 | 0.2 | 0.4 |
| Water | Q.S. | Q.S. | Q.S. |
| Finished Product Viscosity (cps) | 9,380 | 8,470 | 9,460 |
| Expert User Panel[1] |  |  |  |
| Lather Amount (Ratio vs. Comparative Example 1) | 1 | 0.74 | 1.2 |
| Lather Creaminess (Ratio vs. Comparative Example 1) | 1 | 3.0 | 1.9 |
| FCAT Clinical Mildness Testing[2] |  |  |  |
| Difference from Bar Soap Benchmark | −0.34 | −0.25 | −0.46 |

[1]Paired comparison test. Base = 15. Trained lather panelists lather their hands with the product and evaluate for lather amount and creaminess (Scale −3 to 3).
[2]A Forearm Controlled Application Technique for Estimating the Mildness of Personal Cleansers, Ertel, K. D., Keswick, B. H.; Bryant, P. B., 10th International Symposium on Bioengineering and the Skin, June 13–15, 1994, Cincinnati, OH.

Table 4

This table shows the effect of the combination of fatty alcohol and zinc stearate in Example 7.

1. Example 7 has strong lather amount and creamidness versus the Comparative Example 1 and even the fatty alcohol alone formula (Experimental Example 6). The addition of zinc stearate builds on the creamidness boost provided by the fatty alcohol and more than offsets any load the fatty alcohol may put on the lather amount.
2. Example 7 exhibits a draggier rinse feel which is closer to that exhibited in bar soaps. The addition of zinc stearate more than offsets the any additional slick rinse feel contributed by the fatty alcohol.
3. Example 7 improves the rheological profile versus the Comparative Example 1 and even the fatty alcohol alone formula (Experimental Example 6).
4. Example 7 reduces the need for sodium sulfate (thickener) even more than with fatty alcohol alone.

TABLE 4

Preferred Embodiment

|  | Comparative Example 1 | Experimental Example 6 | Example 7 |
| --- | --- | --- | --- |
| Cocamidopropyl Betaine | 5.15 | 5.15 | 5.15 |
| Sodium Laureth Sulfate | 5.8 | 5.8 | 5.8 |
| Sodium Lauroyl Sarcosinate | 0.5 | 0.5 | 0.5 |
| Polyquaternium 10 | 0.1 | 0.1 | 0.1 |
| Polyol Alkoxy Ester | 0.3 | — | — |
| C12/14 Fatty Alcohol | — | 0.5 | 0.5 |
| Zinc Stearate | — | — | 1.5 |
| Pearlescent Agent Pre-Mix: |  |  |  |
| Glycol Distearate | — | 0.25 | 0.25 |
| Sodium Lauryl Sulfate | — | 0.53 | 0.53 |
| Cocamidopropyl Betaine | — | 0.17 | 0.17 |
| Lauramide DEA | — | 0.48 | 0.48 |
| Sodium Sulfate | 2.2 | 0.73 | 0.09 |
| Citric Acid | 0.1 | 0.1 | 0.1 |
| DMDM Hydantoin | 0.2 | 0.2 | 0.2 |
| Tetra Sodium EDTA | 0.1 | 0.1 | 0.1 |
| Fragrance | 0.4 | 0.4 | 0.4 |
| Water | Q.S. | Q.S. | Q.S. |
| Viscosity (cps) | 9,380 | 9,460 | 9400 |
| Expert User Panel[1] |  |  |  |
| Lather Amount (Ratio vs. Comparative Ex. 1) | 1 | 1.2 | 1.42 |
| Lather Creaminess (Ratio vs. Comparative Ex. 1) | 1 | 1.9 | 4.2 |
| Paired Home Use Test[2] |  |  |  |
| Rinse Feel Initially (Low: Draggy, High: Slippery) | N/A | 1.43 | 1.00 |
| Rinse Feel at End of Rinse (Low: Draggy, High: Slippery) | N/A | 1.14 | 0.07 |
| Amount of Lather | N/A | 1.27 | 1.67 |
| Creaminess of Lather | N/A | 1.07 | 1.47 |
| Rheology Panel[3] |  |  |  |
| Stringiness (High: Very Stringy) | 2.45 | 2.09 | 1.45 |

[1]Paired comparison test. Base = 15. Trained lather panelists lather their hands with the product and evaluate for lather amount and creaminess (Scale −3 to 3).
[2]Base = 14. Paired Comparison. Panelists rated the products for the above attributes (Scale −3 to 3).
[3]Panelists poured product out of shower gel bottle and evaluated for "stringiness". A long string of product hangs from the bottle when there is high viscoelasticity. The test compared each of the three products above. Panelists rated the products 1: least string and 3: most stringy.

What is claimed is:

1. A mild personal cleansing composition comprising:
   (a) from about 3 parts to about 10 parts, by weight, of an alkyl ethoxylated sulfate anionic surfactant having an average degree of ethoxylation of at least about 2.0;
   (b) from about 3 parts to about 10 parts of an amphoteric surfactant selected from the group consisting of betaine surfactants, imidazoline surfactants, aminoalkanoate surfactants, and iminodialkanoate surfactants, and mixtures thereof;
   (c) from about 0.1 parts to about 3 parts, by weight of an N-acylamino acid surfactant, or salt thereof;
   (d) from about 0.01 parts to about 0.5 parts, by weight of the composition, of a cationic cellulose ether derivative, wherein said cationic cellulose ether derivative is a polymeric quaternary ammonium salt of hydroxyethyl cellulose reacted with trimethyl ammonium substituted epoxide;
   (e) water from 50 parts to 94 parts;
   (f) from 0.2 parts to 2.0 parts by weight of a C8 to C20 fatty alcohol; and
   (g) from 0.1 parts to 5 parts by weight of a water insoluble salt of C14–C22 fatty acid.

2. A mild personal liquid cleanser composition according to claim 1, wherein said composition comprises:
(a) from about 4 parts to about 8 parts of said alkyl ethoxylated sulfate anionic surfactant having an average degree of ethoxylation of about 2 to about 12;
(b) from about 4 parts to about 8 parts of said amphoteric surfactant selected from the group consisting of:
(i) betaine surfactant of the formula:

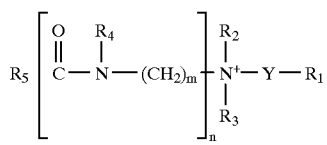

wherein $R_1$ is a member selected from the group consisting of

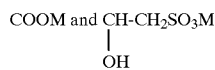

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl ($C_1$ to $C_4$);
m is an integer from 2 to 7;
n is the integer 1 or 0;
M is hydrogen or a cation;
(ii) imidazoline surfactants of the formula:

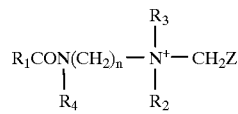

wherein $R_1$ is $C_8$–$C_{22}$ alkyl or alkenyl, $R_2$ is hydrogen or $CH_2CO_2M$, R3 is $CH_2CH_2OH$ or $CH_2CHOCH_2CH_2COOM$, $R_4$ is hydrogen, $CH_2CH_2OH$, or $CH_2CH_2OCH_2CH_2COOM$, Z is $CO_2M$ or $CH_2CO_2M$, n is 2 or 3, and M is hydrogen or a cation; and
(iii) aminoalkanoates of the formula:

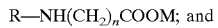

iminodialkanoates of the formula:

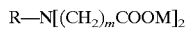

wherein n and m are from 1 to 4, R is $C_8$–$C_{22}$ alkyl or alkenyl, and M is hydrogen or alkali or alkaline metal;
(iv) and mixtures thereof;
and wherein said (a) and (b) have a ratio of about 2:1 to about 1:1.5 on a molar basis;
(c) from about 0.25 parts to about 1 parts, by weight of said N-acylamino acid surfactant, or salt thereof; said (c) selected wherein said N-acyl amino acid surfactant, or salt thereof, and wherein said N-acyl amino acid surfactant is of the formula:

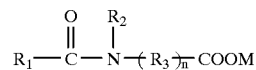

wherein: $R_1$ is $C_8$–$C_{24}$ alkyl or alkenyl:
$R_2$ is —H, $C_1$–$C_4$ alkyl, phenyl, or —$CH_2COOM$;
$R_3$ is —C—$R^4_2$; n is from 1 to 4; $R^4$ is H, $C_1$–$C_6$ alkyl, or $C_1$–$C_6$ alkylester; and M is H or a cation, or a mixture thereof;
(d) from about 0.02 parts to about 0.2 parts said cationic cellulose ether derivative, wherein said cationic cellulose ether derivative is a polymeric quaternary ammonium salt of hydroxyethyl cellulose reacted with trimethyl ammonium substituted epoxide
(e) said water is from about 75 parts to about 90 parts,
(f) from 0.2 parts to 1.0 parts by weight of a C8 to C20 fatty alcohol, and
(g) from 0.5 parts to 2 parts by weight of a water insoluble salt of C14–C22 fatty acid.

3. A mild liquid personal cleansing composition comprising:
(a) from about 3 parts to about 10 parts, by weight, of an alkyl ethoxylated sulfate anionic surfactant having an average degree of ethoxylation of at least about 2.0;
(b) from about 3 parts to about 10 parts of an amphoteric surfactant selected from the group consisting of betaine surfactants, imidazoline surfactants, aminoalkanoate surfactants, and iminodialkanoate surfactants, and mixtures thereof;
and wherein said (a) and (b) have a ratio of about 2:1 to about 1:1.5 on a molar basis;
(c) from about 0.1 parts to about 3 parts, by weight of an N-acylamino acid surfactant, or salt thereof;
(d) from about 0.01 parts to about 0.5 parts, by weight of the composition, of a cationic cellulose ether derivative, wherein said cationic cellulose ether derivative is a polymeric quaternary ammonium salt of hydroxyethyl cellulose reacted with trimethyl ammonium substituted epoxide;
(e) water from 50 parts to 94 parts;
(f) from 0.2 parts to 2.0 parts by weight of a C8 to C20 fatty alcohol; and
(g) from 0.1 parts to 5 parts by weight of a water insoluble salt of C14–C22 fatty acid,
wherein said personal cleansing composition is substantially free of polymeric thickeners and there is little or no alkyl sulfate anionic surfactant.

4. A mild personal liquid cleanser composition as in claim 3, wherein said N-acyl amino acid surfactant is an N-acyl sarcosinate surfactant; wherein said composition comprises from about 4 parts to about 8 parts of said alkyl ethoxylated sulfate, from about 4 parts to about 8 parts of said amphoteric surfactant, from about 0.25 parts to about 1 parts of said N-acyl amino acid surfactant, from about 0.02 to about 1 parts cationic cellulose ether derivative, wherein said cationic cellulose ether derivative is a polymeric quaternary ammonium salt of hydroxyethyl cellulose reacted with trimethyl ammonium substituted epoxide, from about 0.2–1.0 parts fatty alcohol, and from about 0.5 to 2.0 parts of a water insoluble salt of C14–C22 fatty acid.

5. A mild liquid cleanser composition as in claim 4, wherein said fatty alcohol is C12 to C14 fatty alcohol and said water insoluable salt of C14–C22 fatty acid is zinc stearate.

6. A mild personal liquid cleanser composition as in claim 5, wherein said alkyl ethoxylated sulfate has a average ethoxylation of 3 to 4, said amphoteric is cocamidopropyl betaine, and said N-acyl amino acid surfactant is sodium lauroyl sarcosinate.

7. A mild personal liquid cleanser composition as in claim 6, wherein said alkyl ethoxylated sulfate and said cocamidopropyl betaine are in a ratio of about 1.5:1 to about 1:1.5.

8. A mild personal liquid cleanser composition according to claim 1, wherein said composition comprises:
(a) from about 4 parts to about 8 parts of said alkyl ethoxylated sulfate anionic surfactant having an average degree of ethoxylation of about 2 to about 12;
(b) from about 4 parts to about 8 parts of said amphoteric surfactant selected from the group consisting of:
(i) betaine surfactant of the formula:

$$R_5 \left[ \begin{array}{c} O \quad R_4 \\ \| \quad | \\ C-N-(CH_2)_m \end{array} \right]_n \begin{array}{c} R_2 \\ | \\ N^+-Y-R_1 \\ | \\ R_3 \end{array}$$

wherein $R_1$ is a member selected from the group consisting of $$COOM \text{ and } CH-CH_2SO_3M$$
$$\qquad\qquad\quad |$$
$$\qquad\qquad\;\; OH$$

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl ($C_1$ to $C_4$);
m is an integer from 2 to 7;
n is the integer 1 or 0;
M is hydrogen or a cation;
(ii) imidazoline surfactants of the formula:

$$R_1CON(CH_2)_n - \begin{array}{c} R_3 \\ | \\ N^+ - CH_2Z \\ | \\ R_4 \quad R_2 \end{array}$$

wherein $R_1$ is $C_8$–$C_{22}$ alkyl or alkenyl, $R_2$ is hydrogen or $CH_2CO_2M$, R3 is $CH_2CH_2OH$ or $CH_2CHOCH_2CH_2COOM$, $R_4$ is hydrogen, $CH_2CH_2OH$, or $CH_2CH_2OCH_2CH_2COOM$, Z is $CO_2M$ or $CH_2CO_2M$, n is 2 or 3, and M is hydrogen or a cation; and
(iii) aminoalkanoates of the formula:

$$R-NH(CH_2)_n COOM; \text{ and}$$

iminodialkanoates of the formula:

$$R-N[(CH_2)_m COOM]_2$$

wherein n and m are from 1 to 4, R is $C_8$–$C_{22}$ alkyl or alkenyl, and M is hydrogen or alkali or alkaline metal;
(iv) and mixtures thereof,
and wherein said (a) and (b) have a ratio of about 2:1 to about 1:1.5 on a molar basis;

(c) from about 0.25 parts to about 1 parts, by weight of said N-acylamino acid surfactant, or salt thereof; said (c) selected wherein said N-acyl amino acid surfactant, or salt thereof, and wherein said N-acyl amino acid surfactant is of the formula:

$$R_1 - \begin{array}{c} O \\ \| \\ C \end{array} - \begin{array}{c} R_2 \\ | \\ N \end{array} - (R_3)_n - COOM$$

wherein: $R_1$ is $C_8$–$C_{24}$ alkyl or alkenyl:
$R_2$ is —H, $C_1$–$C_4$ alkyl, phenyl, or —$CH_2COOM$;
$R_3$ is —C—$R^4{}_2$; n is from 1 to 4; $R^4$ is H, $C_1$–$C_6$ alkyl, or $C_1$–$C_6$ alkylester; and M is H or a cation, or a mixture thereof;
(d) from about 0.02 parts to about 0.2 parts said cationic cellulose ether derivative, wherein said cationic cellulose ether derivative is a polymeric quaternary ammonium salt of hydroxyethyl cellulose reacted with trimethyl ammonium substituted epoxide, and
(e) from about 0.1 parts to about 0.3 parts antibacterial agent;
(f) from about 0.1 parts to about 15 parts of an oily conditioning agent;
(g) said water is from about 75 parts to about 90 parts;
(h) from 0.2 parts to 1.0 parts by weight of a C8 to C20 fatty alcohol; and
(i) from 0.5 parts 2 parts by weight of a water insoluble salt of C14–C22 fatty acid.

9. A mild personal liquid cleanser composition according to claim 1, wherein said composition comprises:
(a) from about 4 parts to about 8 parts of said alkyl ethoxylated sulfate anionic surfactant having an average degree of ethoxylation of about 2 to about 12;
(b) from about 4 parts to about 8 parts of said amphoteric surfactant selected from the group consisting of:
(i) betaine surfactant of the formula:

$$R_5 \left[ \begin{array}{c} O \quad R_4 \\ \| \quad | \\ C-N-(CH_2)_m \end{array} \right]_n \begin{array}{c} R_2 \\ | \\ N^+-Y-R_1 \\ | \\ R_3 \end{array}$$

wherein $R_1$ is a member selected from the group consisting of $$COOM \text{ and } CH-CH_2SO_3M$$
$$\qquad\qquad\qquad |$$
$$\qquad\qquad\qquad OH$$

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl ($C_1$ to $C_4$);
m is an integer from 2 to 7;
n is the integer 1 or 0;
M is hydrogen or a cation;

(ii) imidazoline surfactants of the formula:

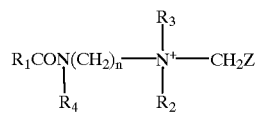

wherein $R_1$ is $C_8$–$C_{22}$ alkyl or alkenyl, $R_2$ is hydrogen or $CH_2CO_2M$, R3 is $CH_2CH_2OH$ or $CH_2CHOCH_2CH_2COOM$, $R_4$ is hydrogen, $CH_2CH_2OH$, or $CH_2CH_2OCH_2CH_2COOM$, Z is $CO_2M$ or $CH_2CO_2M$, n is 2 or 3, and M is hydrogen or a cation; and (iii) aminoalkanoates of the formula:

R—NH(CH$_2$)$_n$COOM; and iminodialkanoates of the formula:

R—N[(CH$_2$)$_m$COOM]$_2$ wherein n and m are from 1 to 4, R is $C_8$–$C_{22}$ alkyl or alkenyl, and M is hydrogen or alkali or alkaline metal;

(iv) and mixtures thereof;
and wherein said (a) and (b) have a ratio of about 2:1 to about 1:1.5 on a molar basis;

(c) from about 0.25 parts to about 1 parts, by weight of said N-acylamino acid surfactant, or salt thereof; said (c) selected wherein said N-acyl amino acid surfactant, or salt thereof, and wherein said N-acyl amino acid surfactant is of the formula:

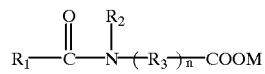

wherein: $R_1$ is $C_8$–$C_{24}$ alkyl or alkenyl:
$R_2$ is —H, $C_1$–$C_4$ alkyl, phenyl, or —$CH_2COOM$;
$R_3$ is —C—$R^4{}_2$; n is from 1 to 4; $R^4$ is H, $C_1$–$C_6$ alkyl, or $C_1$–$C_6$ alkylester; and M is H or a cation, or a mixture thereof;

(d) from about 0.02 parts to about 0.2 parts said cationic cellulose ether derivative, wherein said cationic cellulose ether derivative is a polymeric quaternary ammonium salt of hydroxyethyl cellulose reacted with trimethyl ammonium substituted epoxide, and (e) from about 0.05 parts to about 0.5 parts sensate;

(f) said water is from about 75 parts to about 90 parts;

(g) from 0.2 parts to 1.0 parts by weight of a C8 to C20 fatty alcohol; and (h) from 0.5 parts 2 parts by weight of a water insoluble salt of C14–C22 fatty acid.

* * * * *